United States Patent [19]

Knoll et al.

[11] Patent Number: 5,332,791
[45] Date of Patent: Jul. 26, 1994

[54] POLYISOBUTYLENE HYDROCARBON OR POLYMER CONTAINING A DOUBLE BOND ALLYLIC TO AN END AMINO GROUP

[75] Inventors: Konrad Knoll, Mannheim; Klaus Bronstert, Carlsberg; Dietmar Bender, Schifferstadt, all of Fed. Rep. of Germany

[73] Assignee: BASF Aktiengesellschaft, Ludwigshafen, Fed. Rep. of Germany

[21] Appl. No.: 977,084

[22] Filed: Nov. 16, 1992

Related U.S. Application Data

[62] Division of Ser. No. 744,743, Aug. 14, 1991, Pat. No. 5,212,248.

[30] Foreign Application Priority Data

Aug. 16, 1990 [DE]  Fed. Rep. of Germany ....... 4025961
Sep. 29, 1990 [DE]  Fed. Rep. of Germany ....... 4030914

[51] Int. Cl.$^5$ .................. C08F 110/10; C08F 8/30
[52] U.S. Cl. ................... 525/333.7; 525/376; 525/379; 564/484; 570/189
[58] Field of Search ....................... 525/333.7

[56] References Cited

U.S. PATENT DOCUMENTS 4,068,056  1/1978  Engel ............................ 525/333.7
5,185,401  2/1993  Rendina ......................... 525/130

*Primary Examiner*—Christopher Henderson
*Attorney, Agent, or Firm*—Keil & Weinkauf

[57] ABSTRACT

Hydrocarbons and polymers thereof, of the structure (I)

$$R-C(CH_3)_2-CH_2-C(CH_3)_2-CH_2-CH= CH-CH_2-Cl \quad (I)$$

where R is a hydrocarbon radical, are prepared by reacting corresponding starting materials which contain chlorine bonded to tertiary carbon, of the structure $$R-C(CH_3)_2-CH_2-C(CH_3)_2-Cl \quad (II)$$

with from 1 to 10 moles of butadiene in the presence of a Friedel-Crafts catalyst in a solvent which is inert to the catalyst, and the hydrocarbons or polymers thereof can be reacted in a further step of the process with a compound from the group comprising ammonia, primary or secondary amine or polyamine, amino alcohol, amino ether, hydrazine or hydrazine which is substituted up to three times.

2 Claims, No Drawings

POLYISOBUTYLENE HYDROCARBON OR POLYMER CONTAINING A DOUBLE BOND ALLYLIC TO AN END AMINO GROUP

This is a divisional of application Ser. No. 744,743, filed Aug. 14, 1991 which is now U.S. Pat. No. 5,212,248, issued May 18, 1993.

BACKGROUND OF THE INVENTION

It has been disclosed that isobutene oligomers or polymers with a terminal double bond or terminal chlorine can be prepared by cationic polymerization. In particular, the end groups have structure A $$-CH_2-C(CH_3)_2-CH_2-C(CH_3)_2Cl \qquad (A)$$

Oligomers or polymers of this type can be prepared, for example, by use of the Inifer technique as disclosed in U.S. Pat. No. 4,276,394 with suitable mono- or oligofunctional initiators. This results directly in compounds which do indeed contain chlorine bonded to tertiary carbon as end groups, but the suitability of this for subsequent reactions is low.

Preferred starting materials for subsequent reactions are, by contrast, the adducts of HCl with oligomers or polymers which in turn are prepared by cationic polymerization of isobutene or olefinic $C_4$ cuts. These starting compounds can be obtained, for example using catalysts such as $BF_3$, as described in DE-A 2,904,314. It has also been disclosed that isobutene can undergo cationic oligomerization to give olefins of the structure B or C $$-CH_2-C(CH_3)_2-CH_2-C(=CH_2)-CH_3 \qquad (B)$$

or $$-CH_2-C(CH_3)_2-CH=C(CH_3)_2 \qquad (C).$$

The latter can be converted, in accordance with a not previously published proposal, with HCl into suitable chlorine-containing products. These processes or reactions result initially in compounds which have terminal chlorine bonded to tertiary carbon atoms but whose suitability as such for subsequent reactions is, as mentioned, low. In particular, it is not possible to convert the chlorine substituents into, for example, primary hydroxyl, amino, $-CH=CH_2$ or carboxyl, because HCl is very easily eliminated both in alkaline and in acid media to result in a double bond which has low reactivity and migrates into the interior of the chain, especially in acid medium.

OBJECT OF THE INVENTION

It is an object of the present invention to provide a process which makes it possible to react the chlorine bonded to tertiary carbon so as to produce end groups of high reactivity which can be reacted with a compound from the group comprising ammonia, primary or secondary amine or polyamine, amino alcohol, amino ether, hydrazine or hydrazine which is substituted up to three times.

We have found that this object is achieved in an entirely satisfactory way when the starting materials containing tertiary chlorine are reacted with butadiene in the presence of a Friedel-Crafts catalyst such as $AlCl_3$, $ZnCl_2$, $SnCl_4$, $TiCl_4$, etc., but preferably boron trichloride, in a halohydrocarbon.

SUMMARY OF THE INVENTION

The present invention relates to a process for preparing hydrocarbons and polymers thereof, of the structure (I)

$$R-C(CH_3)_2-CH_2-C(CH_3)_2-CH_2-CH=CH-CH_2-Cl \qquad (I)$$

where R is a hydrocarbon radical, which comprises reacting, a corresponding starting material which contains chlorine bonded to a tertiary carbon, of the structure $$R-C(CH_3)_2-CH_2-C(CH_3)_2-Cl \qquad (II)$$

with from 1 to 10 moles of butadiene in the presence of a Friedel-Crafts catalyst in a solvent which is inert to the catalyst.

Thus, a structure with a very labile chlorine like $R-CH_2C(CH_3)_2-Cl$ is converted into an allylic structure $R-CH_2C(CH_3)_2-CH_2-CH=CH-CH_2-Cl$ which dissociates distinctly less readily. Although stoichiometric addition of butadiene particularly favors the addition of exactly one butadiene unit, some end groups remain unchanged at random. Thus, a suitable procedure is to use 2-3 equivalents of butadiene for quantitative conversion of all the end groups with tertiary chloride, some of the end groups taking up 2 or more molecules of butadiene but having the see good properties and containing the chain termination structure according to the invention. The novel end group is particularly suitable for reactions involving halogen replacement. The allylic chloride makes it possible to introduce a large number of other functionalities in subsequent reactions.

DESCRIPTION OF THE PREFERRED EMBODIMENTS

The starting materials which are advantageously used are isobutene oligomers or polymers which have been prepared by cationic polymerization and contain chlorine bonded to tertiary carbon at one or all chain ends.

A particularly attractive variant of the present process is to employ the same catalyst, eg. $BCl_3$, and the same reactor for the synthesis and polymerization of the required Cl-containing starting compounds and then for the conversion into the compounds (I) according to the invention. The polymerization with $BCl_3$ is described, for example, in U.S. Pat. No. 4,276,394.

Examples of suitable solvents for reactions under Friedel-Crafts conditions are carbon disulfide, nitrobenzene and, in the case of $ZnCl_2$, ethers such as diethyl ether. Chlorohydrocarbons such as dichloroethane, trichloroethylene and methylene chloride are suitable at below 50° C.

A solvent particularly suitable for $BCl_3$ catalysis is methylene chloride. The $BCl_3/CH_2Cl_2$ system can be used for the quantitative synthesis of the required Cl-containing starting compounds (II) as well as the complete conversion thereof into products of the structure (I). Mixtures of chlorinated solvents can also be used, and addition of hydrocarbons can be tolerated within certain limits. The selectivity of the reaction is impaired if the hydrocarbon content is too high.

In the $BCl_3/CH_2Cl_2$ system the reaction generally takes place at a satisfactory rate in the range from $-60°$ to 20° C.; 0° C. or below is preferred.

Not less than 1 equivalent of Friedel-Crafts catalyst should be used per end group, and 3-10 equivalents are advantageous while larger amounts provide no further advantages; since the solvent and catalyst can be recovered at the end, economic considerations play no part.

It is an important technical advantage that the end group of (I) is relatively stable to elimination of HCl in the presence of $BCl_3$, in contrast to tertiary chloride end groups which start to eliminate HCl above $-20°$ C. This makes it possible for costly $BCl_3$ and the methylene chloride to be recovered efficiently by straightforward distillation under reduced pressure. The condensate is suitable for reuse after removal of traces of HCl and unreacted butadiene where appropriate. A high-boiling solvent which is inert under the conditions, such as isooctane or isododecane, can be added before the distillation to reduce the viscosity of the polymer residue.

The products of the reactions in Examples 1-3 which follow were characterized by chlorine determination, gel permeation chromatography and $^1$H-NMR spectroscopy. GPC was carried out on a Waters apparatus with an Ultrastyragel column combination from the same supplier. A refractometer was used for detection and was coupled to a Polymer Standard Service computer evaluation system. Polyisobutene standards were used for calibration, and the eluent was tetrahydrofuran. $\overline{M}_n$ and $\overline{M}_w$ were measured.

The $^1$H-NMR measurements were carried out using a Bruker 200 MHz instrument and a Jeol 60 MHz instrument.

Determination of $-CH_2-C(CH_3)_2-Cl$ End Groups $^1$H-NMR spectroscopy allows a distinction to be made between the protons of the end group and those of the main chain (Polymer Bulletin 3 (1980) 339 and 21 (1989) 5). The average molecular weight $\overline{M}_w$ was calculated from the ratios of the intensities for terminal methyl and methylene groups at $\delta = 1.67$ and 1.96 ppm respectively and non-terminal methyl and methylene groups at $\delta = 1.1$ and 1.4 ppm respectively.

Determination of the $-CH_2-CH=CH-CH_2-Cl$ End Groups

The olefinic protons of the end group are revealed by two characteristic multiplets of the $ABX_2$ spin system at 5.6 and 5.8 ppm. The $CH_2-Cl$ group appears as doublet with bands of weak long-range coupling at 4.0 ppm, while the allylic $CH_2$ group on the polyisobutene side gives a doublet at 2.0 ppm. In the case of the telechelic polymers, the ratio of the intensities of these signals and of the signal from the olefinic initiator sequence at 5.30 ppm provides information on the extent of conversion. Another important indicator of complete conversion is the disappearance of the signals at 1.67 and 1.96 ppm which derive from $-CH_2-C(CH_3)_2-Cl$ groups.

General Experimental Conditions

All the reactions were carried out in dried glass apparatus under nitrogen which had been purified with a solution of butyllithium in 1,1-diphenylethene/mineral oil. Methylene chloride was distilled over triethylaluminum immediately before use, and the isobutene was dried by passing over molecular sieves.

EXAMPLE 1

1-Chloro-5,5,7,7-tetramethyl-2-octene and 1-chloro-9,9,11,11-tetramethyl-2,6-dodecadiene 50 g of 2-chloro-2,4,4-trimethylpentane, 70 ml of dichloromethane and 50 ml of boron trichloride in a 500 ml flask are cooled to $-20°$ C., stirred for 10 minutes, and 19.5 g of butadiene in 30 ml of dichloromethane are added dropwise over the course of 45 minutes; the mixture is then stirred at $-20°$ C. for 3 h. Boron trichloride and dichloromethane are stripped off under 10 mbar, and the residue is mixed with 20 ml of methanol, which is then stripped off. Partition between pentane and water/sodium bicarbonate is carried out, and the pentate phase is distilled to give 9.24 g of 2-chloro-2,4,4-trimethylpentate at 22° C./1 mbar, 22.9 g (33.6%) of 1-chloro-5,5,7,7-tetramethyl-2-octene at 60° C./0.7 mbar, and 7.65 g (8.9%) of 1-chloro-9,9,11,11-tetramethyl-2,6-dodecadiene at 115° C./0.7 mbar. The 19.5 g of residue is composed of multiple butadiene insertion products. The recovered mixture of boron trichloride and dichloromethane can be reused with the same result.

EXAMPLE 2

$-CH_2-CH=CH-CH_2-Cl$-terminated Polyisobutene Macromer 2300 ml of dichloromethane, 130 ml of boron trichloride and 77.4 g of 2-chloro-2,4,4-trimethylpentane are mixed at $-32°$ C. in a 4 l stirred reactor with dry-ice condenser for 5 minutes and 800 ml of isobutene are added dropwise over the course 35 minutes, and polymerization is then carried out for 60 minutes. Subsequently 108 ml of butadiene are added and the mixture is stirred at $-28°$ C. for 4 hours. 300 ml of isooctane are added, and the volatiles are stripped off at $-20°$ C. under reduced pressure. 100 ml of methanol are added dropwise, the mixture is partitioned between pentane and water, and the pentane phase is neutralized with aqueous sodium bicarbonate solution, concentrated and dried at 50° C. under an oil pump vacuum. Cl analysis: 4%; GPC: $\overline{M}_n = 1251$ g/mol, $\overline{M}_w = 2276$ g/mol, $\overline{M}_w/\overline{M}_n = 1.82$.

EXAMPLE 3

Telechelic $-CH_2-CH=CH-CH_2-Cl$-terminated Polyisobutene

The reaction is carried out as described in Example 2. 1700 ml of dichloromethane, 55 ml of boron trichloride, 35.3 g of E-2,5-dichloro-2,5-dimethyl-3-hexene, 600 ml of isobutene and 81 ml of butadiene are employed. Working up is carried out with 50 ml of methanol and 250 ml of isooctane. Cl analysis: 4%; GPC: $\overline{M}_n = 1933$ g/mol, $\overline{M}_w = 2424$ g/mol, $\overline{M}_w/\overline{M}_n = 1.25$.

The hydrocarbons and hydrocarbon polymers of the formula I prepared by the process described above are unsuitable as such for applications as additives to motor fuels and lubricants, components of adhesives and, with telechelic end groups, as prepolymers for polyurea rubbers which are impermeable to water vapor, chemically inert and stable to light. Nevertheless, they become interesting compounds when they are equipped with an allylic amino group in place of the allylic chloride.

This is advantageously achieved when the hydrocarbons or hydrocarbon polymers containing chloride end groups are reacted in a solvent of medium polarity with excess ammonia or a compound with primary or secondary amino groups in the presence of a base, eg. of an alkali metal or alkaline earth metal oxide, hydroxide or carbonate. The amine replaces the chloride by an amino group, with liberation of HCl. The addition of a base liberates the amine with the formation of the corresponding chloride.

Suitable amino compounds are primary or secondary amines, polyamines, amino alcohols, amino ethers, hydrazines, alkylated or arylated hydrazines, hydrazides and hydrazones. If the amine component contains more than one NH linkage it is advantageous to use an excess of amine to avoid multiple alkylation. A 5–15-fold excess of amine is beneficial; ammonia should be employed in an excess of not less than 100 fold.

Preferred bases for binding HCl are magnesium and calcium oxides, calcium hydroxides and sodium and potassium carbonates.

The polarity and amount of the solvent are chosen so that the amine and the hydrocarbon or hydrocarbon polymer form a homogeneous phase, otherwise multiple alkylation occurs when amines with more than one N—H linkage are employed. If this is required, it is also possible to omit a solvent. Particularly suitable solvents are ethers such as tetrahydrofuran, 1,4-dioxane and dimethoxyethane, aromatic compounds such as benzene, toluene or xylenes, long-chain alcohols, and, in principle, chlorohydrocarbons or mixtures of the said solvents. The addition of aliphatic hydrocarbons can be tolerated within limits.

The reaction is advantageously carried out at from 60° to 100° C., in which case it takes 2–6 hours.

If necessary, antioxidants such as 2,6-di-tertbutylphenol and the like can be added during the reaction to suppress discoloration and resin formation.

For the working up, the mixture is diluted with a hydrocarbon such as heptane, isooctane or isododecane, the precipitate is separated off, although this is not indispensable, and extraction is carried out several times with an immiscible polar phase. A suitable polar phase is methanol, 25% strength aqueous isopropanol, 5% strength methanolic or aqueous sodium hydroxide solution. The final extraction should be carried out without addition of a base.

The amino-containing hydrocarbons or polymers according to the invention prepared in this way contain a double bond which is allylic to the amino group. This can be hydrogenated in a conventional manner if required. Examples of suitable catalysts are Raney nickel, palladium black or platinum black; the process is described, for example, in Houben-Weyl, Methoden der Organischen Chemie, volume IV/1c, G. Thieme Verlag, Stuttgart, 1980, page 18/19.

The following remarks apply to Examples 4–14 which follow:

The polymers were stabilized with 0.1% 2,6-ditertbutylphenol. The amines were freshly distilled before use.

The reaction products were characterized by CHN analysis and $^1$H-NMR spectroscopy. The NMR spectra were obtained with a Jeol 60 MHz apparatus.

The determination of $CH_2$—$CH$=$CH$—$CH_2$-amine is based on the appearance of the olefinic protons of the end group as a multiplet at 6.4 ppm. The allylic $CH_2$ group adjacent to the amine nitrogen appears as a doublet at 2.9 ppm, while the signal of the allylic $CH_2$ group on the polymer side appears as a doublet at 1.85 ppm. Protons bonded to nitrogen were identified by H—D exchange with methanol-$d_4$.

EXAMPLE 4

1-Di-n-butylamino-5,5,7,7-tetramethyl-2-octene 10 g (49.5 mmol) of 1-chloro-5,5,7,7-tetramethyl-2-octene, 64 g (495 mmol) of di-n-butylamine and 10 g (248 mmol) of magnesium oxide in 30 ml of THF are refluxed for 4.5 h. The mixture is taken up in 200 ml of hexane, extracted twice with 5% strength methanolic NaOH and once with water and dried at 30° C./1 mbar. Yield: quantitative.

EXAMPLE 5

1-(N-(5,5,7,7-tetramethyl-2-octenyl)-2-aminoethyl)piperazine

In a similar manner to Example 4, 10 g (4.95 mmol) of 1-chloro-5,5,7,7-tetramethyl-2-octene, 64 g (495 mmol) of 1-(2-aminoethyl)piperazine, 10 g (248 mmol) of magnesium oxide and 30 ml of THF are refluxed for 4 h. The mixture is diluted with 300 ml of diethyl ether and extracted once each with 5% strength aqueous NaOH and water, concentrated and dried at 40° C./1 mbar. Yield: quantitative.

EXAMPLE 6

Reaction of Chloroallyl-terminated Polyisobutene Macromer With 1-(2-aminoethyl)piperazine 50 g of 1-chloro-4-polyisobutenyl-2-butene of molecular weight 1,000 (50 mmol), 64.6 g (500 mmol) of 1-(2-aminoethyl)piperazine and 10 g (250 mmol) of magnesium oxide in 25 ml of THF are refluxed for 4 h. The THF is stripped off under reduced pressure, the residue is taken up in 100 ml of hexane and extracted 3× with 40 ml of absolute methanol, and the combined methanol extracts are extracted once by shaking with hexane. The solution is dried at 40° C./0.2 mbar for 3 h. Conversion: virtually quantitative.

EXAMPLE 7

Reaction of Macromer with Hexamethylenediamine

The reaction is carried out in a similar manner to Example 6 with 58.1 g (0.5 mol) of hexamethylenediamine. Conversion: virtually quantitative.

EXAMPLE 8

Reaction of Macromer with Triethylenetetramine

The reaction is carried out in a similar manner to Example 6 with 73.1 g (0.5 mol) of triethylenetetramine. Conversion: virtually quantitative.

EXAMPLE 9

Reaction of Macromer with N-methylethanolamine

The reaction is carried out in a similar manner to Example 6 with 37.6 g (0.5 mol) of N-methylethanolamine. Conversion: virtually quantitative.

EXAMPLE 10

Reaction of Macromer with Diethanolamine

The reaction is carried out in a similar manner to Example 6 with 52.6 g (0.5 mol) of diethanolamine. Conversion: virtually quantitative.

EXAMPLE 11

Reaction of Macromer with Hydrazine Hydrate

The reaction is carried out in a similar manner to Example 6 with 50 g (1 mol) of hydrazine hydrate. Conversion: virtually quantitative.

EXAMPLE 12

Reaction of Macromer with Phenylhydrazine

The reaction is carried out in a similar manner to Example 6 with 54 g (0.5 mol) of phenylhydrazine. Conversion: virtually quantitative.

EXAMPLE 13

Reaction of Macromer with $NH_3$

A 200 ml autoclave is charged with 10 g (10 mmol) of polypher, 10 g (187 mmol) of ammonium chloride and 50 ml of ethylene glycol diethyl ether. The mixture is cooled in dry ice, and 50 ml (2 mol) of liquid ammonia are condensed in. The autoclave is closed and heated at 100° C. for 8 h. After cooling and release of pressure, the ether is stripped off under high vacuum, the residue is taken up in 50 ml of pentane and filtered through kieselguhr with suction and the filtrate is dried under high vacuum. Conversion: virtually quantitative.

EXAMPLE 14

Reaction of Chloroallyl-terminated Telechelic Polyisobutene with 1-(2-aminoethyl)piperazine 50 g (25 mmol) of a chloroallyl-terminated telechelic polyisobutene of molecular weight Mn=2,000 are reacted in a similar manner to Example 6 with 64.6 g (500 mmol) of 1-(2-aminoethyl)piperazine. Conversion: virtually quantitative.

We claim:

1. A polyisobutylene polymer having an end group of the formula

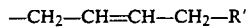
$$-CH_2-CH=CH-CH_2-R'$$

where $R^1$ is a radical formed by reacting a polymer thereof having the structure

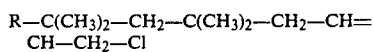
$$R-C(CH_3)_2-CH_2-C(CH_3)_2-CH_2-CH=CH-CH_2-Cl$$

where R is a polyisobutylene radical in a solvent with an excess of ammonia or a compound with primary or secondary amino groups or polyamine, amino alcohol, amino ether hydrazine or substituted hydrazine in the presence of a base.

2. A polyisobutylene polymer as defined in claim 1, where R' is $NH_2$.

* * * * *